(12) United States Patent
Kleinberg et al.

(10) Patent No.: US 8,090,747 B2
(45) Date of Patent: Jan. 3, 2012

(54) METHOD, SYSTEM, COMPUTER-ACCESSIBLE MEDIUM AND SOFTWARE ARRANGEMENT FOR ORGANIZATION AND ANALYSIS OF MULTIPLE SETS OF DATA

(75) Inventors: Samantha Kleinberg, New York, NY (US); Bhubaneswar Mishra, Great Neck, NY (US)

(73) Assignee: New York University, New York, NY (US)

( * ) Notice: Subject to any disclaimer, the term of this patent is extended or adjusted under 35 U.S.C. 154(b) by 677 days.

(21) Appl. No.: 12/124,753

(22) Filed: May 21, 2008

(65) Prior Publication Data
US 2009/0006460 A1    Jan. 1, 2009

Related U.S. Application Data

(60) Provisional application No. 60/939,249, filed on May 21, 2007.

(51) Int. Cl.
*G06F 17/30* (2006.01)

(52) U.S. Cl. ........ 707/803; 707/790; 707/791; 707/792; 707/793; 707/794; 707/795; 707/796; 707/802; 707/944; 707/941; 707/950

(58) Field of Classification Search .............. 707/602, 707/790–796, 802–803, 944, 941, 950
See application file for complete search history.

(56) References Cited

U.S. PATENT DOCUMENTS

| | | | | |
|---|---|---|---|---|
| 5,774,719 A | * | 6/1998 | Bowen | 719/330 |
| 5,933,821 A | * | 8/1999 | Matsumoto et al. | 1/1 |
| 5,956,726 A | * | 9/1999 | Aoyama et al. | 707/755 |
| 6,052,686 A | * | 4/2000 | Fernandez et al. | 707/797 |
| 6,502,112 B1 | * | 12/2002 | Baisley | 715/210 |
| 6,526,410 B1 | * | 2/2003 | Aoyama et al. | 1/1 |
| 6,658,626 B1 | * | 12/2003 | Aiken | 715/205 |
| 6,687,693 B2 | * | 2/2004 | Cereghini et al. | 707/602 |
| 6,741,998 B2 | * | 5/2004 | Ruth et al. | 707/797 |
| 6,757,675 B2 | * | 6/2004 | Aiken et al. | 1/1 |
| 6,839,714 B2 | * | 1/2005 | Wheeler et al. | 1/1 |
| 6,915,282 B1 | * | 7/2005 | Conway et al. | 706/12 |
| 6,928,436 B2 | * | 8/2005 | Baudel | 1/1 |
| 7,353,225 B2 | * | 4/2008 | Dada | 1/1 |
| 7,373,613 B2 | * | 5/2008 | Pohlan | 715/853 |
| 7,747,605 B2 | * | 6/2010 | Narancic | 707/711 |
| 2003/0061200 A1 | * | 3/2003 | Hubert et al. | 707/3 |
| 2004/0093347 A1 | * | 5/2004 | Dada | 707/103 R |
| 2005/0015391 A1 | * | 1/2005 | Pohlan | 707/100 |
| 2005/0216206 A1 | * | 9/2005 | Mossel | 702/19 |
| 2011/0059860 A1 | * | 3/2011 | Gustafsson et al. | 506/10 |

OTHER PUBLICATIONS

Samantha Kleinberg et al., "CLARITY: Algorithms for Semantic Comparison of Time-course Transcriptomic Data", American Association for Artificial Intelligence, 2006, pp. 1-5.

* cited by examiner

*Primary Examiner* — Frantz Coby

(74) *Attorney, Agent, or Firm* — Dorsey & Whitney LLP

(57) ABSTRACT

Exemplary embodiments of system, computer-accessible medium and method can be provided for organizing or analyzing at least two sets of data. The sets of data can be organized and/or analyzed by generating a data structure for the sets of data and comparing the data structure for the at least two sets of data. The data structure can be in the form of a phylogenetic-type tree, and at least one of the sets of the data can include time series data.

26 Claims, 11 Drawing Sheets

Algorithm 1 Align-strings (A,B)
―――――――――――――――――――――――――――

{A and B are strings}
L1      length A
L2      length B
table   array [L1+1][L2+1]
Initialize array to 0
{Fill in first column and first row}
for $i$ = 1 to L1 do
    table [$i$][0] = table [$i$ − 1][0] + score(A[$i$ − 1], GapPenalty)
end for
for $j$ = 1 to L2 do
table [0][ $j$ ] = table [0][ $j$-1]+ score (GapPenalty, B[ $j$ − 1])
end for
{Fill in rest of table}
for $k$ = 1 to L2 do
  for $i$ = 1 to L1 do
    table [$i$ ] [$k$] =
    max of

*table[i − 1] [k] + score (A[i -1], GapPenalty)*
        *table[i − 1 ] [k − 1] + score (A[i − 1], B [k -1])*
        *table[i ] [k-1] + score (GapPenalty, B [k − 1])*
  end for
end for
return table [L1][L2]

F I G. 10

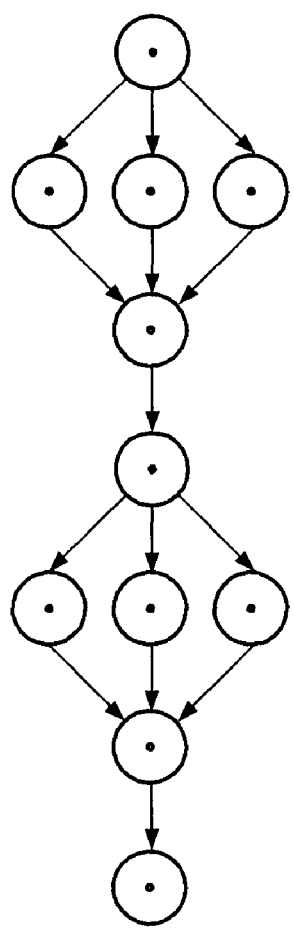
F I G. 11
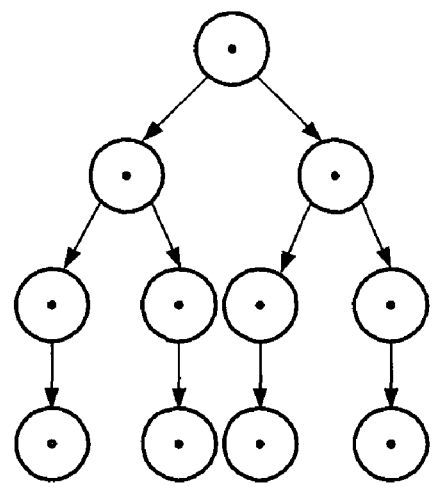
F I G. 12

METHOD, SYSTEM, COMPUTER-ACCESSIBLE MEDIUM AND SOFTWARE ARRANGEMENT FOR ORGANIZATION AND ANALYSIS OF MULTIPLE SETS OF DATA

CROSS-REFERENCE TO RELATED APPLICATIONS

The present application claims priority from U.S. Patent Application Ser. No. 60/939,249, which was filed on May 21, 2007, the entire disclosure of which is incorporated herein by reference in its entirety.

STATEMENT REGARDING FEDERALLY-SPONSORED RESEARCH

The invention was developed with the U.S. Government support from the National Science Foundation under Grant Number CCF 0523851. Thus, the U.S. Government may have certain rights in the invention.

FIELD OF THE INVENTION

The present invention relates to methods, system, computer-accessible medium and software arrangements for comparing two or more sets of data obtained as a function of, e.g., time, drug dose, gene expression, news releases, etc. Such data include, but are not limited to, biological experiments which may be exemplified by time course gene-expression or proteomic data. Exemplary embodiments of the present invention may build upon comparison techniques to organize a large number of sets of data (for example, data derived from experiments) in a database, and may support queries that may identify a dataset that supports or refutes a hypothesis. Applications of exemplary embodiments of the present invention may include, but are not limited to, biological experiments, neural spike-train data, disease progression data, variations in click-stream data for a group of sites on the internet, and/or financial data. In one exemplary embodiment of the present invention, the data may also include an ontological component, or other side information. For example, data which includes a time-based series of job approval ratings may be combined with speech keywords over time. Rules governing the interactions between different types of time series may also be compared and developed. Exemplary embodiments of the present invention may be applied to various data streams that support numerical or logical data which may be queried with respect to set-membership questions.

BACKGROUND INFORMATION

A CL-GoDB system was developed as an interface for the Gene Ontology (GO) database and provided a library of functions for manipulating GO. CL-GoDB has been integrated into GOALIE (a bioinformatics software package developed at NYU), which may be used for the study of time course microarray experiments. GOALIE, in its original incarnation, may analyze time course data and search for a Hidden Kripke Model ("HKM") using a temporal segmentation technique (e.g., one based on information bottleneck based optimization), and may mine the HKM to extract important invariants underlying the experimental data. The HKM may relate to hidden states or possible worlds, transitions among the states, and propositions that label the states. GOALIE may also structure information inherent to HKMs in a Gantt chart format and may provide a visual interface. For example, HKMs or Gantt charts corresponding to, e.g., two related experiments may be compared to discover how their components relate to one another. By comparing Gantt charts using sequence alignment tools, it may be possible to detect aspects of similarity between the two data sets, and hence how "nearby" they are with respect to each other or, e.g., to some other "idealized" experiment. Such distances may also suggest a structure among the datasets (such as a phylogenetic structure) that may be exploited by reflecting it in the structure of the database.

SUMMARY OF EXEMPLARY EMBODIMENTS

Exemplary embodiments of the present invention relate generally to methods, computer-accessible medium, and systems for organizing and analyzing multiple sets of data. For our purpose a computational device may be interpreted as a main-frame, desktop, laptop, pda (personalized digital assistant), cell phone, or other similar devices capable of combining and analyzing data, and a computer-accessible medium may be interpreted as any medium built upon such devices. For example, described herein are computer-accessible medium having stored thereon computer executable instructions for organizing and analyzing at least two sets of input data. When the executable instructions are executed by a processing arrangement, such instructions configure the processing arrangement to create a data structure for the at least two sets of input data; and compare the data structure for the at least two sets of input data, wherein said comparing sets results in organizing and analyzing the at least two sets of input data.

Described herein are also exemplary embodiments of methods, systems and computer-accessible medium for organizing and analyzing at least two sets of input data, by possibly creating a data structure for the at least two sets of input data; and comparing the data structure for the at least two sets of input data. For example, the comparing sets can result in organizing and analyzing the at least two sets of input data.

Exemplary embodiments of methods, systems and computer-accessible-medium for organizing and analyzing at least two sets of input data are also provided. In one exemplary embodiment, a processing arrangement may be provided which, when executed, is configured to create a data structure for the at least two sets of input data; and compare the data structure for the at least two sets of input data, wherein said comparing sets results in organizing and analyzing the at least two sets of input data.

These and other objects, features and advantages of the present invention will become apparent upon reading the following detailed description of embodiments of the invention.

BRIEF DESCRIPTION OF THE DRAWINGS

Further objects, features and advantages of the invention will become apparent from the following detailed description taken in conjunction with the accompanying figures showing illustrative embodiments of the invention, in which:

FIG. 10 is an exemplary computer code listing for a procedure for comparing and/or aligning data representations, e.g., Gantt charts;

FIG. 11 is an exemplary inferred causal structure with arrows denoting genuine causal inferences;

FIG. 12 is an exemplary inferred causal structure with arrows denoting genuine causal inferences.

Figure 1:
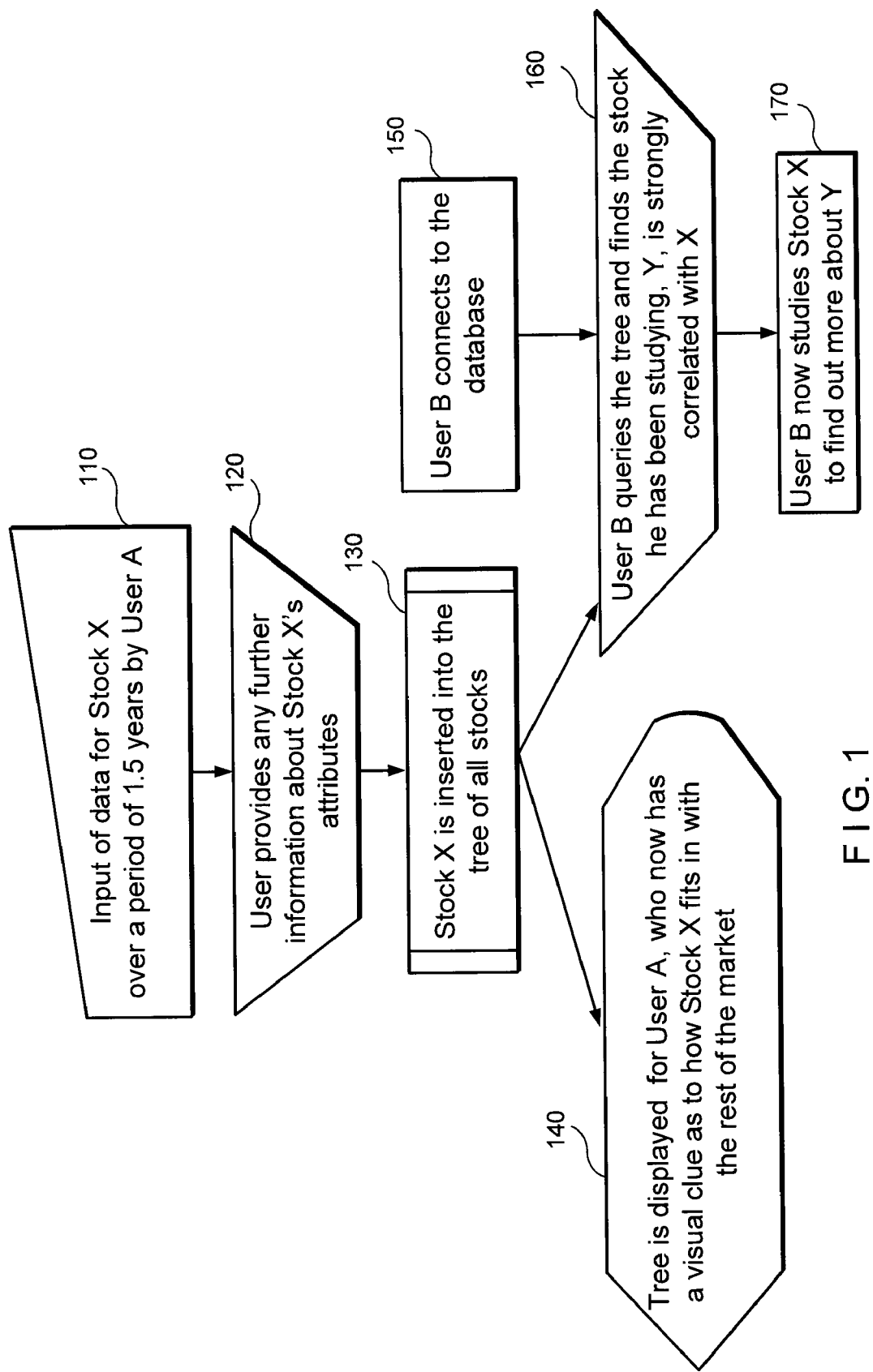
FIG. 1 is an exemplary flow diagram illustrating analysis of stock market data in a system described herein. As exemplified in FIG. 1, the system may be accessed by multiple users.

Throughout the figures, the same reference numerals and characters, unless otherwise stated, are used to denote like features, elements, components or portions of the illustrated embodiments. Moreover, while the subject invention will now be described in detail with reference to the figures, it is done so in connection with the illustrative embodiments. It is intended that changes and modifications can be made to the described embodiments without departing from the true scope and spirit of the subject invention

DETAILED DESCRIPTION OF EXEMPLARY EMBODIMENTS

Exemplary embodiments of the present invention may organize large amounts of data, where exact relations among these sets of data may not be completely known a priori. The data may be generated, for example, from a plurality of experiments which may be related experiments. Comparisons among the sets of data, which may further include a control and/or test data set, may be performed, e.g., using an alignment of their corresponding Gantt charts.

Using such comparisons, it may be possible to organize a large number of data sets (which may include, e.g., both past and present time points) based on, e.g., alignment/comparison and/or a data repository. For example, having prior data sets and being able to analyze them in concert with current data sets may be of significant value. Further, techniques which use additional information from new data may lead to adjustment of accepted paradigms and may modify viewpoints and interpretations of a subject or data being studied.

Applications for such comparison and analysis of data sets may include, e.g., disease discovery based on, for example but not limited to, a microarray or deep-sequencing-based gene expression data, financial tracking (based on for example but not limited to) stock market data or other financial and market data, etc. Such applications may seem to be disparate, but may have a similar structure. For example, gene expression microarray data may provide two types of information: numerical values of the gene expression levels, and names of the genes together with the terms they are annotated with in a controlled vocabulary such as the Gene Ontology.

Stock market data may provide similar information, for example, on the up or down movements of the price for a stock each day (or on a finer timescale) as well as a categorization (such as technology, energy, etc). The inferences made in each case may be similar, even when the knowledge bases are unrelated.

In a biological setting, e.g., when dealing with gene expression data, such comparison may be accomplished in two procedures: summarizing activity of Gene Otology ("GO") terms over time windows (to create the Gantt charts—e.g., bar graphs representing the data over time); and aligning sequences of activity between pairs of experiments.

Database structures used in accordance with exemplary embodiments of the present invention may exploit abstractions available based on raw data and ontological annotations. Further annotations of the data may also be made. For example, exemplary embodiments of the present invention may be used to correlate time series stock market data with time series news data (such as, e.g., news keywords, blog tags, and/or web search keywords), or gene expression data may be correlated with disease diagnoses. Further, an individual data set may be defined by multiple separate time series. For example, financial data may include time series information on, e.g., price changes as well as trading volume.

The present invention is referred to as CLARITY, an abbreviation for Common Lisp data Alignment ReposITorY. The components of the present invention include, but are not limited to:

1) A common format for input data;
2) A database to hold the input data;
3) An integrated comparison procedure with the database; and
4) An interface for user interaction with the above three components.

In an exemplary embodiment of the present invention, one or more users may provide or upload input data, e.g., data sets, and optionally fill out a form containing information about the input data via, e.g., a simple form or series of checkboxes. The input data may be inserted into a database and placed into a data structure which acts as a repository for the input data, e.g., multiple data sets. The data structure of this repository may be, e.g., a phylogenetic-type tree, including all data sets or experimental conditions to be analyzed. Alternate data structure, (e.g., representations of the data) may be possible including, e.g., any network structure, graph, cladogram, etc. For example, the lengths of edges in a phylogenetic-type tree may represent a distance of nodes from one another. When analyzing disease-related data, e.g., specific breast cancer cell lines may be organized as a subset of breast cancer and then of all cancers. Thus, distance in the tree between such cell lines may be less than a distance between breast cancer cell lines and prostate cancer cell lines. The tree may be re-optimized (e.g., emptied and rebuilt) at certain intervals, e.g., after a predetermined number (such as 100 or 500) of inserts. Thus, the representation of the data (e.g., the act) may be thought of as continually learning and re-grouping data, such as patient-specific data, but each individual insert into it may remain fast. Accordingly, in an exemplary embodiment, the data base is a repository for both the input data and representations of the data.

One exemplary comparison technique may be based on Gantt charts, which may provide an overview of an entry's activity over a window of time. For example, each bar in a Gantt chart of stock market data may represent a stock's activity (e.g., whether it traded up or down) over the period of, for example, a week. By summarizing such overviews into strings and aligning them to other overviews, e.g., in other datasets, it may be possible to produce an exemplary comparison score for, e.g., produce a measure of similarity across, datasets. Then, by compiling these scores, such as by averaging scores for all terms between two datasets, an overall similarity score may be assigned to a pair of datasets. Performing this technique for multiple datasets and creating a tree based on the results may allow a quantification of how far apart certain data sets, e.g., illnesses, stocks, or other types of information, are from one another.

Such exemplary comparison techniques may provide an annotated database, where it may further be possible to make queries and inferences. As nonlimiting examples, queries may be of the following type, "Display all highly active genes in white women over 45 who have chronic fatigue syndrome (CFS,) or "Display the most common categorization for stocks behaving similarly to the one the user has just specified." Operations such as diagnosing patients based on their microarray data may then be possible. Providing a tunable value that represents the confidence in a categorization may allow certain invariants to be inferred such as, e.g., "You entered a patient who you believe has A, but their genes are behaving like that of a person with B, so treat them with C, since that cured B," or "You were very confident in the diagnosis of the patient you entered; due to that confidence, we believe 10 other people in the database, entered with no diagnosis, have the same illness." Such implementation may also be used to assign, for example, more or less weight to industry sector information when comparing stock price data.

Exemplary embodiments of the present invention may include the following exemplary components:
A) A common format for input data (which may be suitable for multiple types of data);
B) A database with at least one data structure (e.g., a phytogenic type tree, any network structure, a graph, a cladogram, a gantt chart, etc.);
C) An integrated comparison procedure for organizing at least one data structure after insertion of input data into the database;
D) An interface for user interaction with the above three components. In an exemplary embodiment, the interface may optionally include one or more of the following:
i) A graphical user interface(GUI) that allows access to the database;
ii) A visualizer to display the data structure;
iii) Tools for graphical comparison and navigation of the data structure's components; and
iv) further optimization and additions to the GUI and related navigation tools Various subsets of the above listed components may be assembled in exemplary embodiments of the present invention.

Exemplary Input Data.

The exemplary input data may preferably include tab or comma separated files, where the first row may contain, e.g., window or time period start and end times in decimal format, for example, where 1.0=one hour. Subsequent rows may begin with, e.g., an identifier followed by pairs of numerical values and optional sets of genetic information. Data rows for biological data may be of the form, for example: "cell cycle," −1.3, cdc16 SAP185, 2, PLM2 POG1; where "cell cycle" may be an identifier, −1.3 and 2 are numerical values which may describe, e.g., activity of the identifier during the $1^{st}$ and $2^{nd}$ windows respectively, and cdc16 and SAP185 may annotate "cell cycle" during window 1 and PLM2 and POG1 during window 2.

Creation of Exemplary Data Structure, e.g., a Gantt Chart.

Gantt charts are data structures which may be employed in exemplary embodiments of the present invention. The data may be structured such that it may be broken into rows of discrete items, where the items may have a form such that there is a unique identification of the item, a series of columns including numerical components of the item, and optional further information such as, e.g., categorization, in the following columns. The numerical components may be arranged into overlapping "windows," such that, for example, if the data ranges from time i to time j there may be windows of size 2 having the form i to i+3, i+3 to i+5 . . . j−2 to j. The windows may be of any appropriate size; the value of 2 is used only for illustration. The windows need not be delineated in a physical representation of the data, as they may be a logical formulation imposed on the data later for simplification.

A Gantt chart may be created by the following exemplary operations:

Loop for each item in the dataset {
   with w being the chosen size of the time window;
   Collect the average for each collection of columns of width w in the set of columns describing the data's numerical components (i.e. starting from a column referred to as 0, average 0 to w, w to 2w and so on until no more columns with numerical data remain);
   For each average computed{
      convert the number to a character representing its level of activity as it relates to 0. Characters used are U (greater than zero), D (less than zero), N (exactly zero), and I denoting that there is no activity of the entry at that point in time.};
   Create an object and store the entry's Unique ID as well as describing string (as defined by the character representations of the numerical averages)
}

Data may not always be centered on zero, though that restriction may be imposed. Two primary data structures may be used to store the aligned items. One exemplary structure may contain a reference to the stored set of data or experiment and may have three slots: one for a Unique ID, one for a string describing the item's activity, and one for numerical data. The second data structure may contain a slot to hold a reference to an object of the type described above, as well as a slot for a score of the alignment. This second structure may be inserted into a hash table during alignment.

Comparison of Exemplary Structures.

Once the data is provided in a format such that numerical values may be described by a string as shown, e.g., in the description of the creation of the Gantt chart herein above, the data may be compared to other such data items. Comparing a pair of data items may include, e.g., iterating over an intersection of the data items contained in each data set. In the case of microarray gene expression data, this may be performed by iterating over the terms annotating the genes in the dataset. The describing string for each term in this intersection may then be aligned using an exemplary procedure such as (e.g., a standard pairwise alignment procedure as described), (e.g., by Needleman and Wunsch), to provide a comparison score.

An exemplary procedure which may be used in exemplary embodiments of the present invention is shown in FIG. 10. The scoring matrix used for this comparison may be altered depending on the type of data used. The score (e.g., similarity) between pairs of data may depend, in addition to an alignment score on other factors. Nonlimiting examples include:

$$Score=Alignment(StringX,StringY)-\rho*|NumericalX-NumericalY|2+\kappa*Jaccard(GenesX, GenesY),$$

where

Jaccard(A,B)=Intersection(A,B)/Union(A,B).

Parameters ρ and κ having values of zero, for example, may correspond to only the alignment score being considered. Increasing these values may assign an increasing weight to the difference in exact numerical values and genes regulating the terms. In biological and non-biological examples, for example, gene data may be replaced with any other data sets to be analyzed.

An additional feature to a standard exemplary procedure for scoring an alignment may be inclusion of a measure of how much the items differ (e.g., a representation of an exact numerical distance), which may be weighted such that this measure may influence the results to a varying degree. Instead of looking at the distance between an "A" and a "C," as may be done in genetic alignment procedures, the data may preferably be represented by letters U, D, N and I, which may represent up, down, neutral/normal and inactive, respectively. In general, a score or penalty for aligning one character to another may be determined. This may include, e.g., using measures such as: aligning up to down=−2, aligning up to normal/neutral=−1, etc. As each term is aligned it may then be stored in a hash table, with the hash key corresponding to a score associated with the pair of characters. This temporary data structure may facilitate sorting and/or manipulation of the intermediate alignments. After iterating over the intersection, the resulting alignments of terms may be compiled into a single alignment. This may be achieved, e.g., by averaging the scores of the individual alignments to form a single score for the data pair.

Exemplary Phylogenetic Tree. A tree representing the relationships between the input data entries in the database may be a binary tree in which the entries are leaves and their relationships are represented by the internal nodes of the tree as well as its edges. The internal nodes may contain consensus sequences, which may be the statistically most correlated portions of their immediate descendants. They may also be defined by the exactly equivalent portions of the two children of the consensus node. The lengths of the edges of the tree may indicate the distance between nodes and their parents.

Insertion into Exemplary Data Structure.

Insertion of the data item into the database may involve a standard database insert as well as determining an entry's relationship to other current database members. This may be performed, e.g., by using a pre-order traversal of the phylogenetic tree, which may be binary, and determining at each step whether the entry to be inserted is more similar to the left or right child of the current node, where such similarity may be based on alignment of the entry to the consensus sequence or describing string at the node. This exemplary technique may be further improved by using a procedure that includes deeper nodes in the decision to move left or right. For example, as described in k-ply look ahead procedures, the entry to be inserted may be aligned to all descendants of the left/right children of the current node to a depth of k and may move left or right depending on the maximum similarity score. Such techniques are illustrated, e.g., in FIGS. 2 and 3.

Optimization of Exemplary Data Structure

After a certain number of inserts, the data structure (e.g., phylogenetic tree) may be reformed. Reforming may include, e.g., removal of all nodes and redetermination of the tree from the beginning. This may be done, e.g., using procedures such as neighbor joining.

Exemplary Substructure Information Extraction

Exemplary Substructures within Data Structures may be analyzed. For example, within a main phylogenetic tree, it may be useful to break up the whole tree into smaller subtrees. This exemplary technique may be used to identify, e.g., subtypes of a disease, groups of similarly behaving stocks, and/or blogs discussing similar topics. One method of identifying such subtrees may be based on, e.g., three parameters such as: minimum tree size, maximum tree size, and a threshold for a minimum similarity score at the subtree's root. For example, a very large subtree may not be very informative, as there may be more variation between its members, but a tiny subtree with only a few nodes may also not provide much information. Finally, it may be preferable to have a cohesive tree—e.g., similar to itself—and a threshold for the similarity score of its root node may be used to achieve this. A subtree may include smaller sub-trees (perhaps including those that violate size requirements), and further requirements may be imposed on the subtrees including, e.g., a limitation that all consensus nodes in subtrees have a minimum score.

FIG. 1 shows a flow diagram of an exemplary embodiment of a method for organizing or analyzing multiple sets of data, e.g., stock data according to the present invention. This exemplary method may be performed by a processing arrangement, for example, but not limited to, a computer that includes a microprocessor or another processing device, and using instructions stored on a computer-accessible medium (RAM, ROM, hard drive, or other storage device). For example, the processing arrangement can receive data for Stock X over a period of 1.5 years 110, which may be input into a database by a first user, e.g., User A. User A may optionally provide further information about Stock X in step 120. In step 130, the data for Stock X is inserted into a data structure, e.g., a phylogenetic-type tree structure, containing all stock data within the database. In step 140, the tree may be displayed for User A, such display providing User A with a visual analysis as to how Stock X compares to the rest of the stock data (e.g., the market). Optionally, in step 150, a second user, e.g., User B may connect to the database, e.g., through either the same or another processing arrangement. In step 160, User B may query the phylogenetic-type tree to find that Stock Y is strongly correlated with Stock X. In step 170, User B may study Stock X to find out more about Stock Y.

Figure 2:
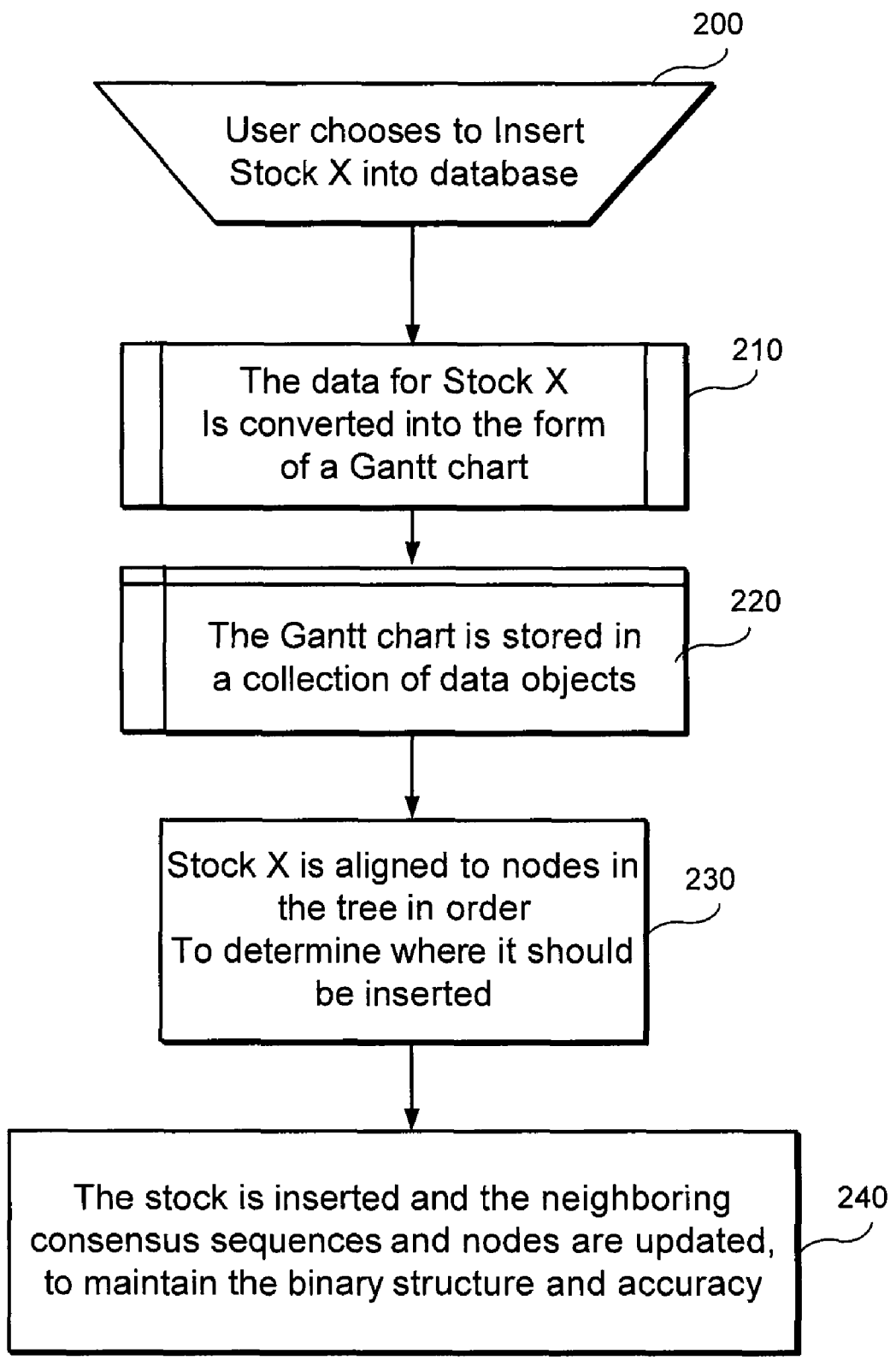
FIG. 2 is a flow diagram illustrating a process of inserting input data into a database as described herein. Also shown in FIG. 2 is an exemplary comparison procedure as described herein.

In FIG. 2 which shows a flow diagram of another exemplary embodiment of the method according to the present invention, a user may choose to insert Stock X into a database in step 200, via, e.g., the processing arrangement. In step 210, the data for Stock X may be structured in the form of a Gantt chart. In step 220, the Gantt chart may be stored, e.g., in the same database, as a collection of data objects. In step 230, Stock X is aligned to nodes in a phylogenetic-type tree in order to determine where it should be inserted in the phylogenetic-type tree. In step 240, the data for Stock X is inserted and the neighboring consensus sequences and nodes are updated to maintain the binary structure and accuracy.

Figure 3:
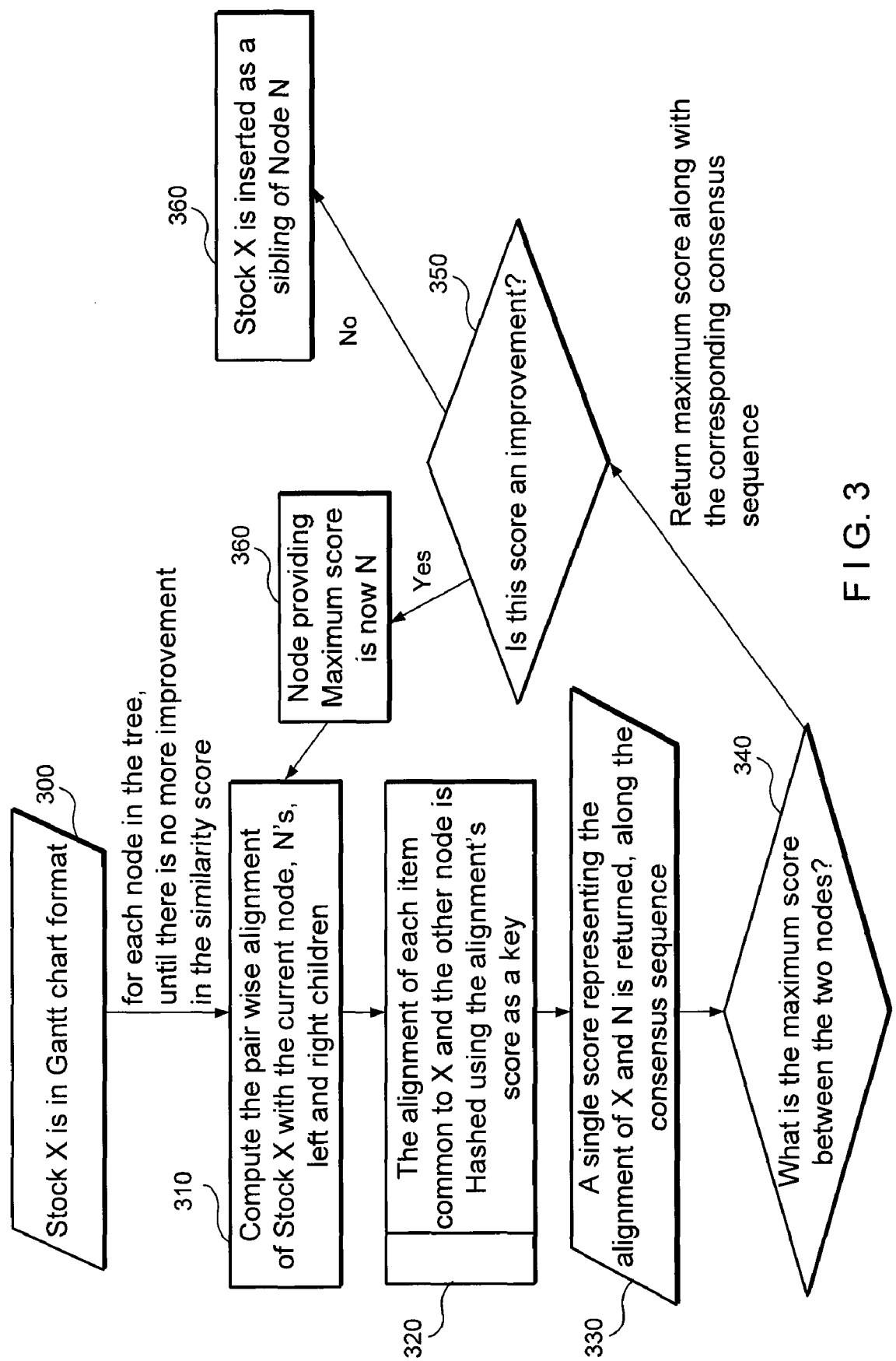
FIG. 3 is a flowchart exemplifying a comparison procedure as described herein.

In FIG. 3, which shows a flow diagram of yet another exemplary embodiment of the method according to the present invention, an exemplary procedure or method for alignment is illustrated. In step 300, Stock X in Gantt chart format is input into a database. In step 310, a pairwise alignment of Stock X with a current node, N's, left and right children is performed. Step 310 is performed for each node in a phylogenetic-type tree until the similarity score is no longer improved by such comparison. In step 320, the alignment of each item common to Stock X and other nodes is hashed using the alignment score as a key, and in step 330, a single score representing the alignment of Stock X and N is returned along with a consensus sequence. In step 340, the maximum score between two nodes is determined. The maximum score and the corresponding consensus sequence is returned. In step

350, it is determined whether the score is an improvement. If that is the case, the node providing the maximum score becomes N in step 360. Additionally, steps 310-360 are repeated until the score is no longer an improvement. If the score is not an improvement, the data for Stock X is inserted as a sibling of Node N in step 370.

The processing arrangement described herein above which is configured to execute one of more of the exemplary procedures and/or method shown in FIGS. 1-3 may be provided with an input arrangement, which may include, e.g., a wired network, a wireless network, the internet, an intranet, etc. In addition, the processing arrangement may be provided with an output arrangement, which may include, e.g., a wired network, a wireless network, the internet, an intranet, etc.

Figure 13:
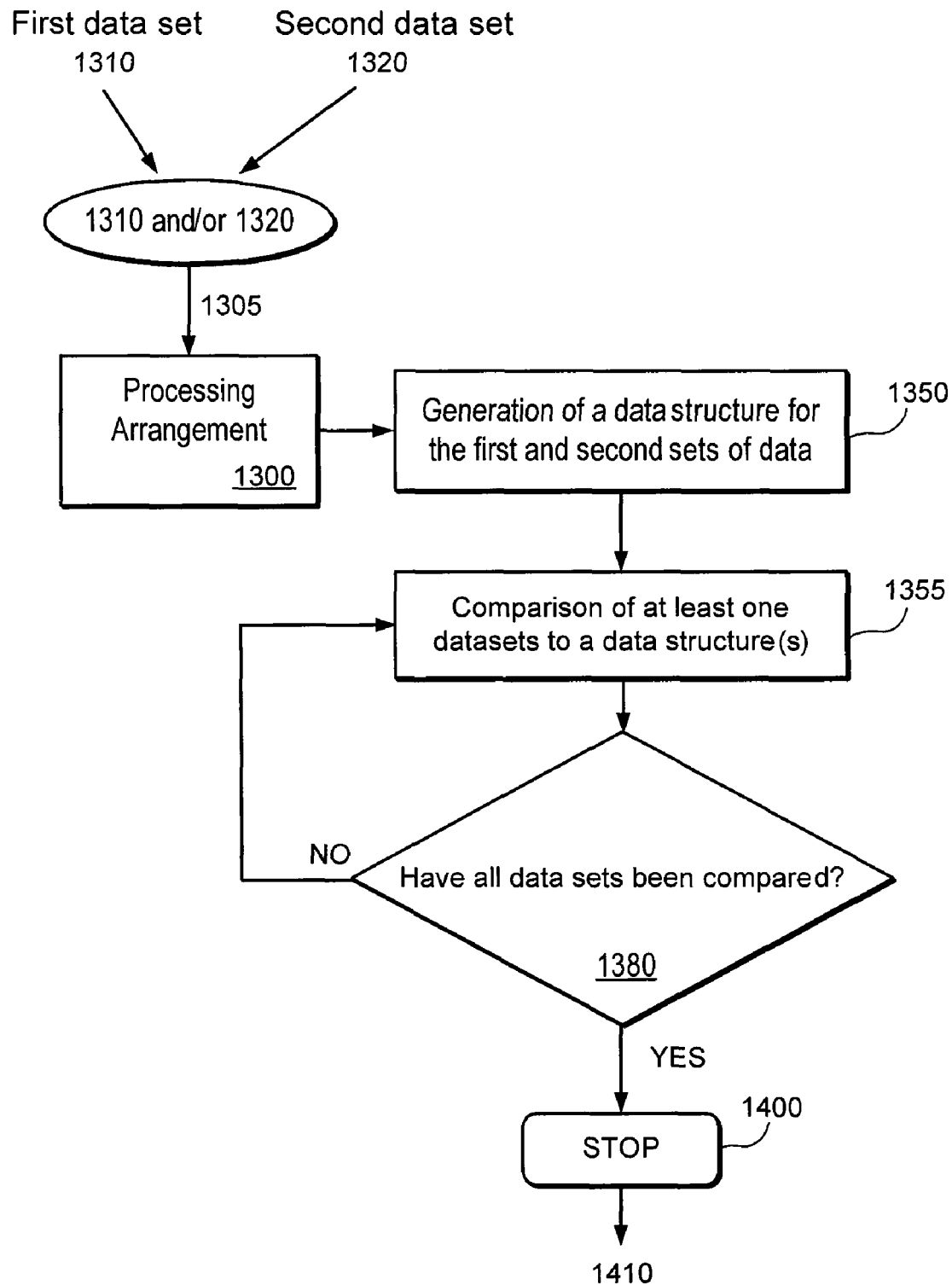
FIG. 13 is a combination of a system diagram and a further flow diagram in accordance with another exemplary embodiment of the present invention.

FIG. 13 shows a diagram of a further exemplary embodiment of a combination of a method and a system for organizing or analyzing multiple sets of data according to the present invention. The exemplary method may be performed by the exemplary system which can include a processing arrangement 1300 such as, but not limited to, a computer with a microprocessor or another processing device, and can be used with instructions provided on a computer accessible medium. For example, the processing arrangement can receive a first set of data 1310 and a second set of data 1320. In step 1350, the processing arrangement generate a data structure for the first and second sets of data. In step 1380, the processing arrangement can determine whether all datasets have been compared. If not, another dataset may be compared to the data structure in step 1355. If all datasets have been compared, the exemplary method stops in step 1400.

As shown in FIG. 13, the processing arrangement 1300 may be provided with and/or include an input arrangement 1305, which may include a communication network, e.g., a wired network, a wireless network, the internet, an intranet, etc. In addition, the processing arrangement 1300 may be provided with an output arrangement 1410 which may include, e.g., a wired network, a wireless network, the Internet, an intranet, etc.

Rule Generation.

An exemplary embodiment described herein may also include generating rules. One example of an association rule, e.g., for shopping transaction data may be "20% of transactions that contain apples also contain bananas," where 20% may be referred to as a confidence in the rule, and the percentage of all transactions containing both apples and bananas would be the support for the rule. One solution which may be introduced is the Apriori procedure, which involves finding events occurring either simultaneously or in a related way, with certain rules determining this relatedness. This type of pattern finding may be used for mining associations and sequential patterns.

An event sequence may refer to, e.g., a series of (label, time) pairs, where the event labels may be obtained from some finite alphabet describing types of events. An episode may refer to a group of events occurring together. This may indicate either that they occur simultaneously (as in parallel episodes), or that they form a serial or an even more complex pattern. For example, there may be two event sequences, but rules may be limited to a small subset of all possible rules, as described herein below. A common feature of such techniques may be that in order for a pattern of length n+1 to be frequent, its sub-pattern of length n must also be frequent. By using this rule, the number of patterns to be tested may be reduced in later stages of the procedure, and the representation of the data may also be simplified as each iteration rules out more patterns. At each step, the patterns of length n+1 being tested may be referred to as candidates, as these patterns may turn out to be frequent, but at this earlier stage of the analysis they may be treated as hypotheses.

In an exemplary potential rule-testing phase in accordance with exemplary embodiments of the present invention, rules may have two components: a hypothesis A->B (e.g., if A then B), and the evidence A, and B. In a simple form, rules may have the structure A->B but they may also grow to rules such as A->(B^C) (if A then B and C) or any other desired temporal formula. For example, using one exemplary dataset such as stock market data, a time series of market data may be extracted, as well as time series news data and test rules of the form "If news event A, then stock B has response C" where C may include, for example, that the price goes up or down or may take on a certain predicted numerical value. Using a Bayesian odds-likelihood formulation, posterior odds of the rules being tested may be computed. This may provide an estimate of how well one event may be predicted after occurrence of another event. Such techniques may be used for, e.g., finding patterns in news stories and the response of the financial markets, finding connectedness among neurons from neural spike-train data, or correlating presidential speeches with job approval ratings. or other devices (e.g., mobile phone, personal digital assistant, etc.) with embedded computational modules etc.

A simple exemplary rule generation procedure may include determining rules with one left side and one right side, where the left side may be used, e.g., to predict an event and the right side may be, e.g., the event being predicted. This type of formulation may be applied, for example, to correlating news keywords with stock price changes. An example of such a rule generation procedure is:

For each h in the set of hypotheses H, add h to candidates (a hypothesis may be a firing neuron, a keyword, or an ontology term);

For i=1 to n (where n is a threshold defining the max pattern size), repeat:

For c in candidates test c->e, for each event e in the set of events E, by counting the instances when the rule does and does not hold, and calculating the rule's posterior odds;

If the rule's odds are greater than the threshold, add it to the set of rules;

Else, remove c from candidates;

Then, for each c in candidates, add each h in hypothesis to a copy of the rule, making a new set of candidates, each of length i+1. Another exemplary embodiment of the rule generation procedure can solve the problem formalized as follows: given a set of numerical time series data representing events for which it may be hypothesized that there may exist a causal structure, underlying relationships forming this structure may be inferred. A relationship between two events means that knowing one allows the explanation or prediction of the other. These inferred relationships may be of the form "c causes e within time t with probability p" where c is a logical rule, e is an atomic proposition and t is a window of time.

In another exemplary embodiment, causality rules may be formulas for causal relationships. Such causality rules are non-deterministic and are defined in terms of probabilities, where cause and effect are events. Two assumptions may be made. For example, it may be stipulated that causes are temporally prior to their effects. This assumption may be limiting in some ways, but it is may be justified by its relevance and its ability to significantly aid the inference process. Further, causes may raise the probabilities of their effects and describe how they may be inferred.

For exemplary causality rules, non-deterministic relationships may be represented in a probabilistic extension of CTL (Computation Tree Logic), PCTL. Alternatively, causal rules may use a logic such as UTSL (Unified Temporal Stochastic Logic), which incorporates statistical hypothesis testing, which may be extended for multiple hypothesis testing. Input may be represented data as follows. First, a finite set of atomic propositions, A, each denoting an event in the dataset is obtained. Rules may be comprised of atomic propositions a in the universe A, propositional logical connectives (such as ¬, ^, ∨) and modal operators denoting time and probability. There are two types of formulas in PCTL: path formulas and state formulas, which may be defined inductively as:

Each atomic proposition is a state formula;

If $f_1$ and $f_2$ are state formulas, so are $-f_1$, $(f_1 \hat{} f_2),(f_1 f_2)$, $(f_1 \rightarrow f_2)$;

If $f_1$ and $f_2$ are state formulas, and t is a nonnegative integer or ∞, then $f_1 U^{\leq t} f_2$ and $f_1 U^{\leq t} f_2$ are path formulas; and If f a path formula and p is a real number with $0 \leq p \leq 1$, then $[f]\geq_p$ and $[f]>_p$ are state formulas.

Standard path quantifiers A ("for all paths") and E ("for some future path") and temporal operators F ("eventually holds"), G ("holds for entire future path"), U ("for two properties, p holds until q holds", and q holds at some point), W (weak until or unless "p holds until q holds" but with no guarantee that q will ever hold), and X ("at the next state") may be used. In addition, a "leads to" operator may be used. A leads-to operator may be defined as:

$$f_1 \leadsto_{\geq p}^{\leq t} f2 \equiv AG[(f1 \rightarrow F_{\geq p}^{\leq t} f2)] \quad (1)$$

Possible transitions from each state to each other state may be updated to reflect actual transitions and probabilities from the given input data.

In terms of PCTL formulas, four exemplary types of causes may be defined, namely prima facie, spurious, genuine, and supplementary.

Exemplary causal relationships may be defined in terms of the time that elapses between cause and effect. If c occurs at time t and e occurs at time t', the relationship may be characterized by the time that elapses between them, [t'-t]. That is, if a hypothesis is that after c becomes true, e may be true with probability at least p in less than t time units, the following: $c \leadsto_{\geq p}^{<t} e$ may be written.

Thus, the relationship between cause and effect may be described in terms of the transition probabilities between states. Prime facie, or potential, causes may defined as follows: c is a prima facie cause of e iff:

$F_{\geq 0}^{\leq \infty} c$
$c \leadsto_{\geq p}^{\leq t} e$
$F_{<p}^{\leq \infty} e$ There may be a number of transitions between c and e, as long as the probability of that path is $\geq p$ and it takes time $\leq t$. The probability of a path may be defined as the product of the transition probabilities along the path.

In some cases, input data may be in the form of domain specific knowledge and the amount of time between cause and effect in terms of a window of time may be desired. Such a window of time in which e occurs (say, between t1 and t2 inclusive) after c occurs may be represented by:

$$c \leadsto_{\geq p}^{\geq t2, \leq t1} e \quad (2)$$

For example, in an exemplary embodiment, causal relationships may be inferred from at least 3 variables, where states from which it is also possible to transition to an e state may be examined to determine if they could provide more information than just c.

Testing for spurious relationships may occur using the following method. First, with X being the set of prima facie causes of E, for each $\chi \in X$, the predictive value of c in relation to x may be calculated. In other words, the probability of transitioning to an e state from a $c \hat{} x$ state versus a $\bar{c} \hat{} x$ state may be determined. If these probabilities are very similar, then c might be a spurious cause of e. However, there may only be one such x, while there may be a number of other x's where there is a large difference in the computed probabilities. One example of such a case is where there are two genuine causes of a common effect.

To address this issue, the average difference in probabilities for each prima facie cause of an effect in relation to all other prima facie causes of the effect may be determined.

$$\text{With } \epsilon_x = P(e|c \wedge x) - P(e|\bar{c} \wedge x) \quad (3)$$

the following may be determined:

$$\epsilon_{avg} = \frac{\sum_{x \in X} \epsilon x}{|X|} \quad (4)$$

Thus, for each prima facie cause, a value of its average effectiveness as a predictor of its effect may be obtained. Further, this $\epsilon_{avg}$ may be used to determine whether c is a valid cause.

It may be further defined that:

A cause, c, may be an $\epsilon$-spurious cause of an effect, e, if: c is a prima facie cause of e and $\epsilon_{avg} < \epsilon$.
where $\epsilon$ is a pre-defined threshold or may be determined using statistical methods.

Further, c, a prima facie cause of an effect, e, may be a genuine cause of e if it is not an $\epsilon$-spurious cause of e.

As a nonlimiting example, input data on smoking (S), yellow stained fingers (Y) and the incidence of lung cancer (C) in people who smoke and have stained fingers may be provided. Assuming that smoking and staining of fingers both occur prior to the development of lung cancer, it will be found that likely both S and Y are prima facie causes of C. However, looking at $P(C|S \hat{} Y) - P(C|S \hat{} \bar{Y})$, testing Y's contribution to C, this difference is likely to be found nearly zero (accounting for the possibility that there may be some other reason for stained fingers that is also a cause of lung cancer). In that case, provided these are the only events in the experiment, it may be determined that S is a genuine cause of C, and Y may be a spurious cause of E.

A cause may not be immediately ruled out as being spurious if there only exists another cause that is an equally good predictor of the effect, as long as with regard to other causes, it is still causally relevant to the effect. As noted before, these may be independent causes of a common effect, or they may be supplementary causes. That is, in combination the causes may predict their effects better than each cause alone.

Additionally, it may be defined that two prima facie causes c and d are supplementary causes of an effect e if:

$F_{\leq 0}^{\leq \infty} c \wedge d$
$c \hat{0} d \leadsto_{\geq p''}^{\leq t''} e$
$p'' > \max(p', p)$
where $t'' \leq (t'+t)$, $c \leadsto_{\geq p}^{<t} e$, and $d \leadsto_{\geq p'}^{<t'} e$ For example, c and d may be logical formulas. The same or exemplary formulas for spuriousness may apply, and it is possible that supplementary causes may be defined in terms of some $\epsilon$ as well, possibly ensuring that the conjunction of the two causes adds significantly to predicting the effect.

The problem can become one of determining when the model satisfies the formulas of interest. Described herein is exemplary logic and/or procedure which may be used to test for causal relationships. Model checking may involve testing whether a given system satisfies some temporal logic formula. If the problem may be encoded in such a framework, then conventional methods and/or procedures for hypothesis generation and refutation may be used.

In order to reason about causal structures in time-course data, a subset of temporal logic, Computation Tree Logic (CTL) may be used. CTL is a branching time logic, where the future may be along any number of possible paths and formulas are checked over a directed graph called a Kripke structure. PCTL extends this logic to reason about systems with soft-deadlines. The formulas in PCTL are interpreted over structures, where a structure is a quadruple: $\langle S, s^i, T, L \rangle$, such that S is a finite set of states $S^i \in S$ is an initial state T is a transition probability function, T: $S \times S \rightarrow [0, 1]$ such that for all s in S:

$$\sum_{s' \in S} T(s, s') = 1 \quad (5)$$

L is a labeling function assigning atomic propositions to states, $$L: S \rightarrow 2^A \quad (6)$$

The exemplary truth values of formulas for specific structures may be defined in terms of their satisfaction relations as shown herein. The satisfaction relation, $s \models_K f$, means that state formula f is true in state s in structure K. Then, $s \models_K \alpha$ (state s satisfies atomic proposition $\alpha$) if $\alpha \in L(s)$. Relations for $\neg, \wedge, \vee$, and $\rightarrow$ are then defined as normal. The path satisfaction relationships, $\sigma \models_K f$ means that the path $\sigma$, satisfies the path formula f in model K. Accordingly, the following path relations may be obtained:

$\sigma \models_K f_1 U^{\leq t} f_2$ iff $\exists i \leq t$ such that $\sigma[i] \models_K f_2$ and $\forall j: 0 \leq j < i: (\sigma[i] \models_K f_1)$ (strong until)

$\sigma \models_K f_1 W^{\leq t} f_2$ iff $\sigma \models_K f_1 U^{\leq t} f_2$ or $\forall j: 0 \leq j \leq t: \sigma[j] \models_K f_1$ (weak until)

$s \models_K [f] \geq_p$ if the $\mu_m$-measure of the set of paths $\sigma$ starting in s for which $\sigma \models_K f$ is at least p $s \models_K [f] \geq p$ if the $\mu_m$-measure of the set of paths $\sigma$ starting in s for which $\sigma \models_K f$ is greater than p where the $\mu_m$-measure is the sum of probabilities over the set of paths from s that satisfy f.

One may define exemplary causal relationships in terms of probabilistic temporal logic formulas and encode datasets as logical models. Then, the problem of inference may be one of generating these causal formulas and then using model checking to determine whether the model satisfies them.

As an initial matter, since complex PCTL formulas may be generated, inferences may be restricted in terms of the type of formulas tested and the length of time between cause and effect. The exemplary formula of interest may vary depending on the data being analyzed as well as background knowledge. Described herein is an exemplary embodiment of a method and/or a procedure that may be used when there is no prior knowledge. The time between cause and effect may be restricted to be either one time unit or some fixed length of time. A further exemplary restriction may be to look only for formulas that are conjunctions of events. In the simplest exemplary case, where there is only one unit of time between cause and effect and only conjunctions of events are being tested, a set of formulas may be used to test each event as a possible prima facie cause of each other event. Then, the prima facie causes of common effects may be evaluated to determine whether any are supplementary causes (replacing the two original prima facie causes in the set of causes with the resulting conjunction of causes). Further, for each set of prima facie causes of an effect, spuriousness may be tested as described herein.

The complexity of testing whether the model satisfies the formula may also be analyzed as follows. The complexity of forming the model can depend on the upper bound on time windows, $|A|$, and the number of time points in the data set.

With these exemplary methods and/or procedures, the exemplary idea may be that states may be labeled with subformulas that are true within them, incrementally building the full formula. The time complexity of this algorithm may be shown to be $O(t_{max}*(|S|+|E|)*|f|)$, where $t_{max}$ is the maximum time parameter in the formula, S is the number of states, E the number of transitions with non-zero probability and f is the size of the formula (the number of propositional connectives and modal operators, plus the sum of the sizes of the modal operators in the formula).

As described herein, embodiments within the scope of the present invention include computer-accessible medium for carrying or having computer-executable instructions or data structures stored thereon. Such computer-accessible medium may be any available media that can be accessed by a general purpose or special purpose computer. By way of example, and not limitation, such computer-accessible medium may comprise RAM, ROM, EEPROM, CD-ROM or other optical disk storage, magnetic disk storage or other magnetic storage devices, or any other medium which can be used to carry or store desired program code means in the form of computer-executable instructions or data structures and which can be accessed by a general purpose or special purpose computer. When information is transferred or provided over a network or another communications link or connection (either hardwired, wireless, or a combination of hardwired or wireless) to a computer, the computer properly views the connection as a computer-accessible medium. Thus, any such a connection is properly termed a computer-accessible medium. Combinations of the above should also be included within the scope of computer-accessible medium. Computer-executable instructions comprise, for example, instructions and data which cause a general purpose computer, special purpose computer, special purpose processing device or other devices (e.g., mobile phone, personal digital assistant, etc.) with embedded computational modules etc. to perform a certain function or group of functions.

Those skilled in the art will appreciate that the invention may be practiced in network computing environments with many types of computer system configurations, including personal computers, hand-held devices, multi-processor systems, microprocessor-based or programmable consumer electronics, network PCs, minicomputers, mainframe computers, and the like. The invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

EXAMPLES

Example 1

Exemplary Application of CLARITY to Stock Data

Exemplary embodiments of the present invention may be used, e.g., to find patterns and/or relationships in financial time-based data series, such as stock market data. To illustrate this technique, the following example provides an analysis of a dataset based on the Standard and Poors (S&P) 500 stock index during the month of July 2002.

The data includes closing prices during 22 trading days for the 509 stocks that were part of the S&P 500 at some point during July 2002. Data for each trading day was provided in a single file, containing all stock symbols in the S&P 500 for that day, their closing price, and other information. This data was then transformed such that for each stock, there was a series of 22 (date, price) pairs. Then, a series of pairs containing numerical values comparing each price to the price of the prior day was generated as a string. Such strings were generated as follows: if the price at the end of a certain day is greater than the prior day, that day is represented by "U" for that stock; if the price is less than the prior day, it is represented by "D"; if there is no change, it is represented by "N" and if that stock was not traded or not part of the S&P 500 that day, it was represented by "I." Numerical values representing each day's percent change were also generated.

After this exemplary procedure was applied to the data, each stock was represented by a string such as, e.g., "UDDDINNUNDIDN", where each letter corresponds to a particular date. Such representation may be referred to as a Gantt chart for the stock. Then, each stock's numerical data, Gantt chart and other associated information were assembled into a database. The data included the stock's full name, GICS, and industry sector.

Figure 4:
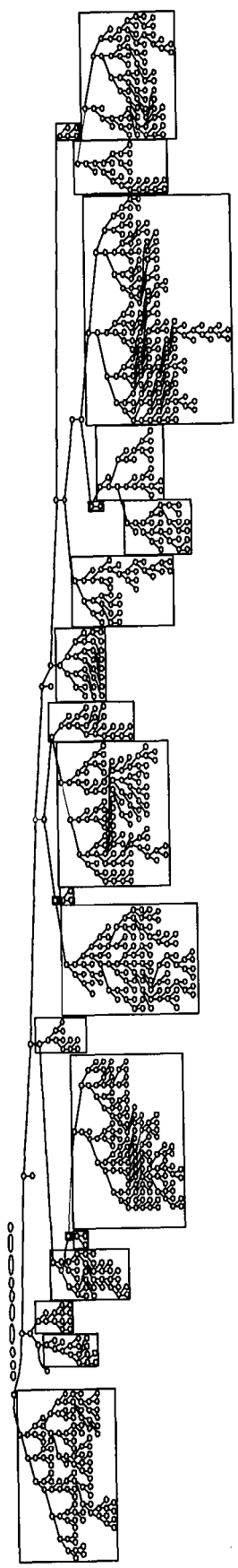
FIG. 4 is an exemplary data structure resulting from analysis of a dataset based on the Standard and Poors 500 stock index during the month of July using a system as described herein.

As each stock's Gantt chart was inserted into the database, it was aligned to other Gantt charts which had already been inserted. This was performed using the procedure described herein above. Such alignments resulted in a phylogenetic-like tree, as shown in FIG. 4. The tree is color coded using the GICS (Global Industry Classification Standard). Some trees are divided strongly by sector. For example, there is a subtree which includes primarily Information Technology stocks. This result was interesting, as the month studied exhibited a lot of activity among technology stocks.

Figure 5:
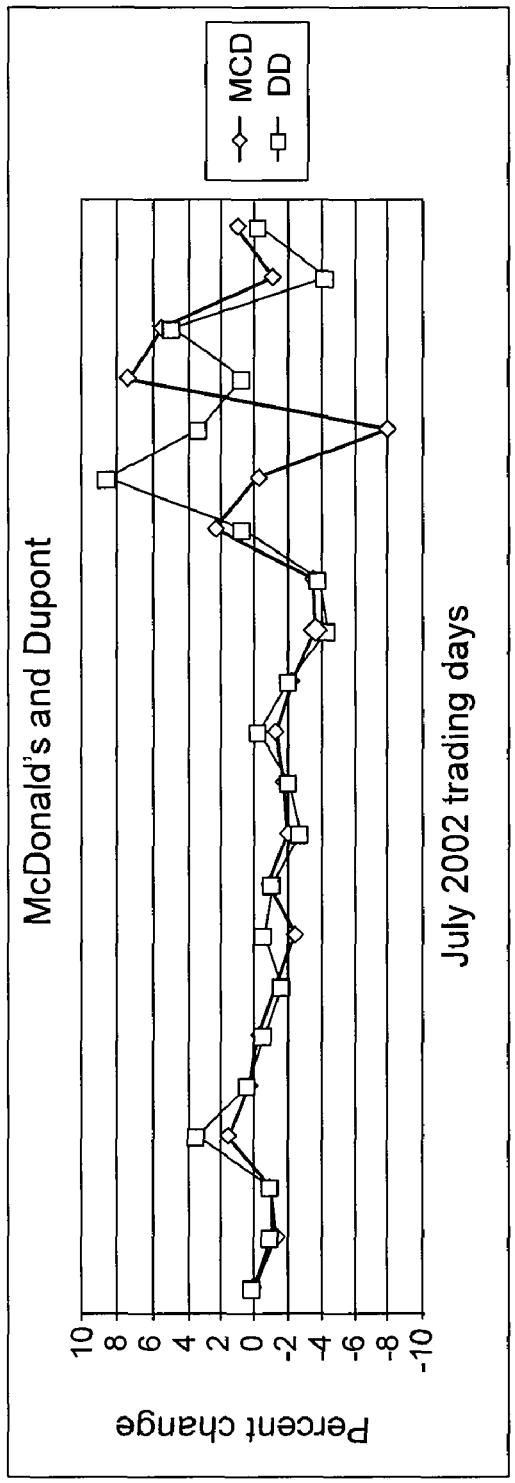
FIG. 5 is a time-based plot of exemplary input data in the form of stock data.
Figure 6:
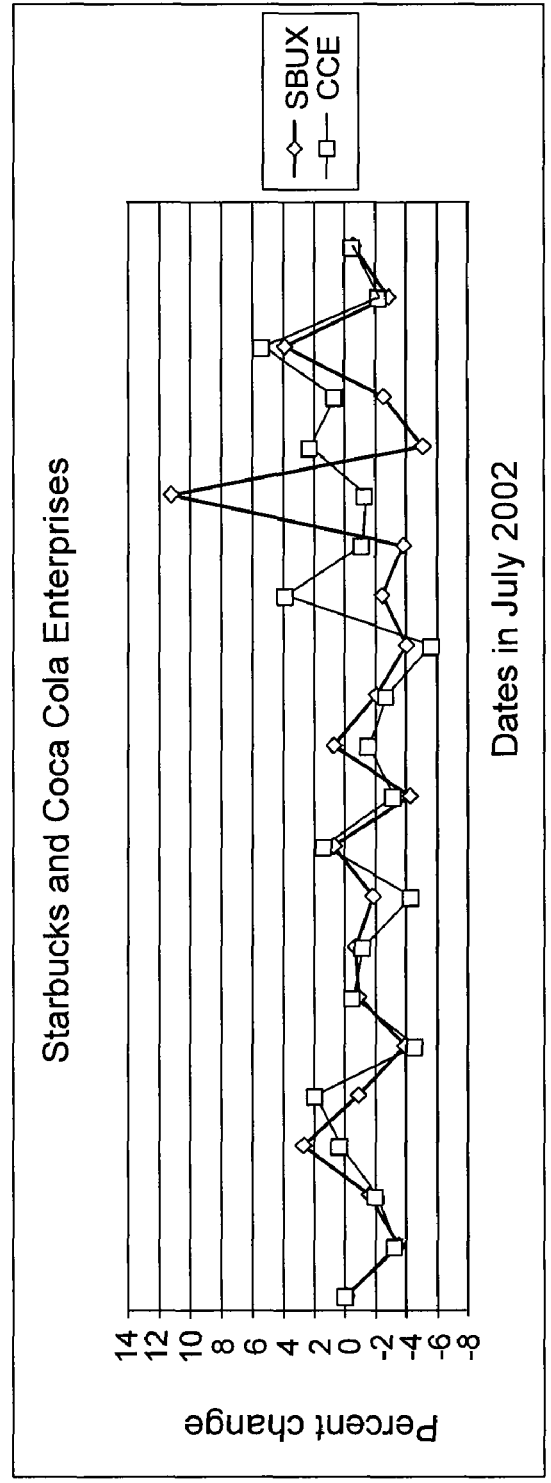
FIG. 6 is a time-based plot of exemplary input data in the form of stock data.
Figure 7:
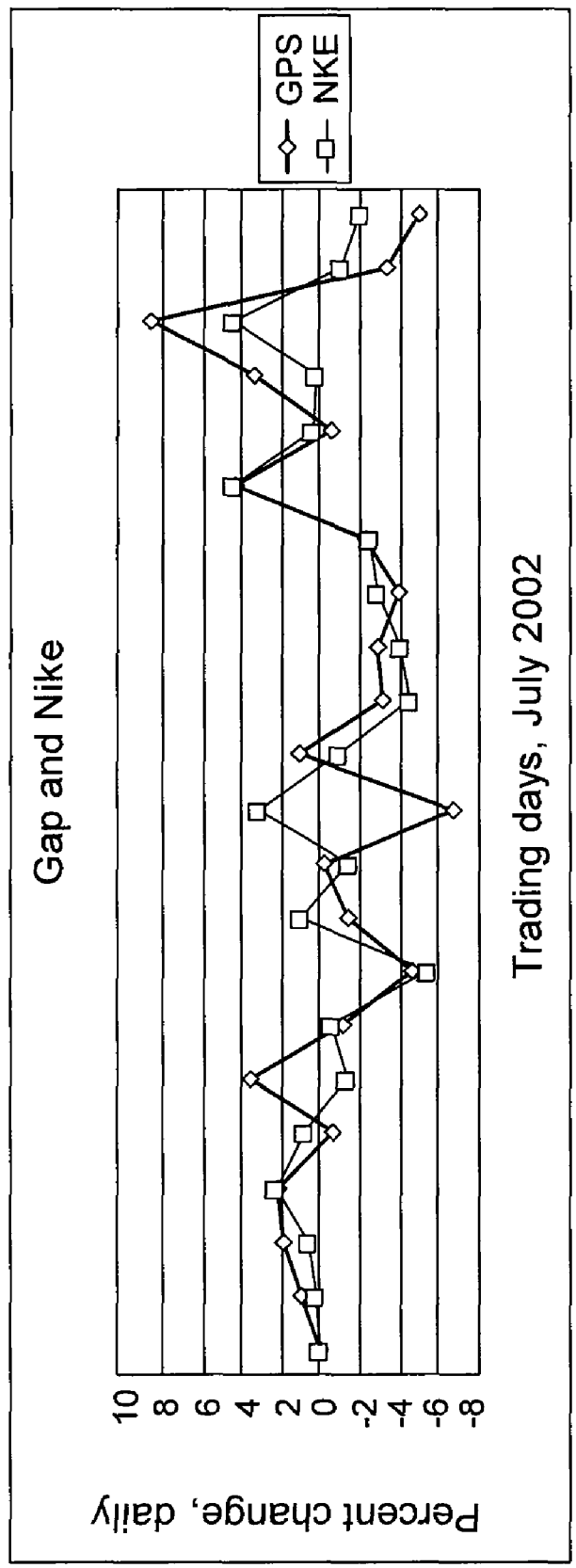
FIG. 7 is a time-based plot of exemplary input data in the form of stock data.
Figure 8:
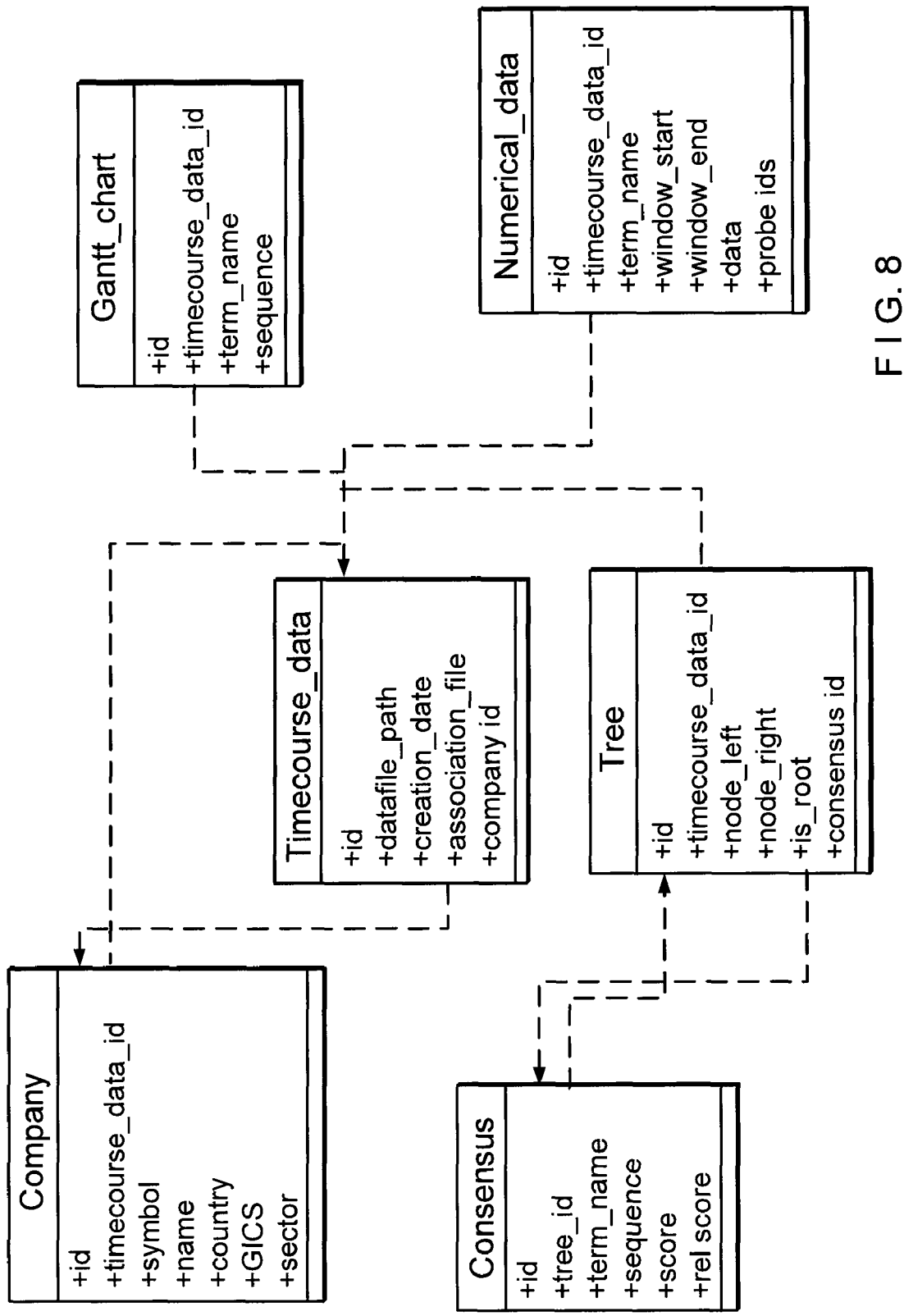
FIG. 8 is an exemplary embodiment of a database structure for finance data.
Figure 9:
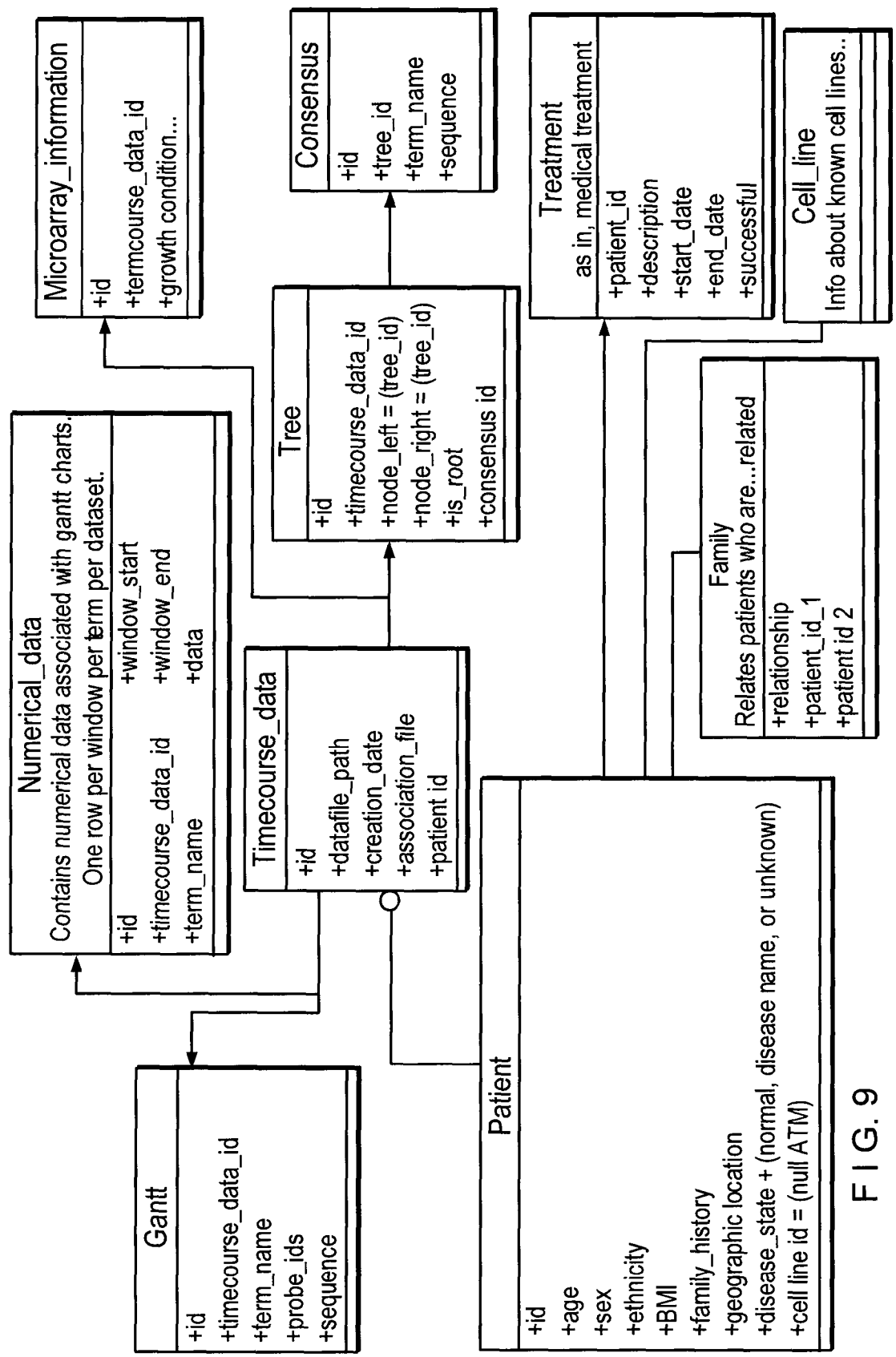
FIG. 9 is an exemplary embodiment of a database structure for medical data.

Other information revealed by the present analysis include pairwise and group relations between stocks. After examining a correlation with the S&P 500 stocks as a whole, it was observed that such relationships were stronger, and not simply a reflection of the overall market. One such relationship was observed between MCD (Mc Donald's) and DD (Dupont), as shown in FIG. 5. A strong correlation was discovered automatically, using software in accordance with exemplary embodiments of the present invention. It was observed that these two stocks had the same overall pattern activity, with some interesting behaviors. When DD went up 8% on one day, MCD began going down, and went down 8% the following day. When examining news reports to explain this, it was found that both companies had announced positive earnings, and that MCD announced it was in the black for the first time in seven quarters. Thus, it was interesting that the stock went down so sharply. News articles during that time period also mentioned that the market was "desperate for good news." It was also observed that, over multi-year periods, MCD and DD maintained a correlation similar to that shown in FIG. 5. They appear to be correcting themselves—e.g., moving together, then diverging briefly (with one going up when the other goes down) and coming back together. This type of relationship was also found for pairs such as SBUX (Starbucks) and CCE (Coca-Cola Enterprises), shown in FIG. 6, as well as for GPS(Gap) and NKE (Nike), shown in FIG. 7.

Example 2

Exemplary Causal Rule Generation for Simulated Neural Spike Trains

Causal rules were generated for 20 data sets simulating neural spike trains, each embedded with a set of causal relationships. The data was provided as part of the 4th KDD workshop on Temporal Data Mining (publicly available at http://people.cs.vt.edu/-ramakris/kddtdm06/). Each data set consisted of 26 neurons, and 100,000 firings of the neurons. At each moment of time, a neuron can fire randomly (the probability of this depending on the noise level selected for the data set), or could have been be triggered by one of the neurons that caused it to turn on. Each neuron may also have been caused to fire by multiple neurons, and cause multiple neurons to fire in turn. There was known to be a window of time, 20 to 40 time units, after one neuron fired in which it may have triggered another. The 20 data sets represented 5 different causal structures, with 2 sets of 100,000 firings generated with each structure for a low and high noise level. The structures were all DAGs and ranged from long chains of neurons, to binary trees. Two of the causal structures are shown in FIGS. 11 and 12.

For these data sets, the known time windows were used to narrow down the potential causes of a neuron's firing. In other words, P(E|C) where E occurs between 20 and 40 time units after C was examined. So, condition 2 of prima facie causality was replaced with $c \leadsto_{\geq p}^{\geq 20, \leq 40} e$. Looking at each data set individually, 100% of the causal relationships in the low noise data sets and 92% of the causal relationships in the high noise data sets were identified. After determining $\epsilon_{avg}$ for each prima facie cause of effects with multiple potential causes, it was discovered that in cases where one event had multiple distinct causes (e.g. Y in FIG. 11) none were ruled out by this method, though other incorrect causes were. After considering only relationships identified in both data sets generated for a causal structure and a given noise level, all incorrect relationships were eliminated. This result may also be achieved by using a sufficiently high $\epsilon$, though a comparatively low value was used. Two of the inferred structures are described herein in FIGS. 11 and 12.

In prior analysis of the data generated from the structure shown in FIG. 12, where only for frequent logic formulas were examined, both D and E were found to be causally related to H and I, and both F and G were found to be causally related to J and K. However, using this method, testing for spuriousness with $\epsilon_{avg}$, the genuine causes were correctly inferred.

The exemplary structure shown in FIG. 11, would seem to pose a problem, given the many-to-many relationships. However, in both the low and high noise datasets, A, B and C were all identified as genuine causes of Y, while all other factors (including Z) were ruled out. Similarly, E, F and D were equally relevant to P, while other factors had very low causal relevance, as measured by $\epsilon_{avg}$. In general, A, B, C had higher causal relevance to Y than E, F, D did to P (particularly in the high-noise dataset), due to the fact that the pattern is not always repeated in its entirety, and there were fewer examples of the later relationships in the series than there were of the earlier ones.

The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. In addition, to the extent that the prior art knowledge has not been explicitly incorporated by reference herein above, it is explicitly being incorporated herein in its entirety. All publications referenced above are incorporated herein by reference in their entireties.

What is claimed is:

1. A non-transitory computer-accessible medium having stored thereon computer executable instructions for at least organizing or analyzing at least two sets of data which, when the executable instructions are executed by a processing arrangement, configure the processing arrangement to perform a procedure comprising:
(a) generating a data structure for the at least two sets of the data, wherein at least one of the sets of the data includes time series data; and
(b) comparing the data structure for the at least two sets of the data, wherein the comparison of the data structure results in one of the at least two sets of data being at least one of organized or analyzed;
wherein the data structure is a Gantt chart, and is generated by the operation of:
Loop for each item in a dataset {
    with w being a chosen size of the time window, and
    Collect the average for each collection of columns of width w in a set of columns describing the data's numerical components, starting from a column referred to as 0, average 0 to w, w to 2w and so on until no more columns with numerical data remain),
    For each average computed{
        convert a number to a character representing its level of activity as it relates to 0, and characters being used are U that are greater than zero, D that are less than zero, N that are exactly zero, and I denoting that there is no activity of the entry at that point in time},
    Create an object and store the entry's Unique ID and describing string as defined by a character representations of numerical averages }.

2. The computer-accessible medium of claim 1, wherein the data structure includes, in addition to the Gantt chart, a phylogenetic-type tree.

3. The computer-accessible medium of claim 1, wherein the processing arrangement is further configured to reoptimize the phylogenetic-type tree.

4. The computer-accessible medium of claim 1, wherein the comparison of the data structure comprises
(i) iterating over at least one intersection of the data contained in each of the sets, and
(ii) providing a comparison score for the comparison, wherein the comparison is provided to detect a similarity between each of the sets.

5. The computer-accessible medium of claim 1, wherein the processing arrangement is further configured to extract substructures within the data structure.

6. The computer-accessible medium of claim 1, wherein the processing arrangement is further configured to generate at least one rule using a rule generating procedure associated with the data structure.

7. The computer-accessible medium of claim 6, wherein the processing arrangement is further configured to test the at least one rule with a model checking procedure.

8. The computer-accessible medium of claim 7, wherein the model checking procedure uses at least one of Computational Tree Logic, Probabilistic Computational Tree Logic, or Unified Temporal Stochastic Logic.

9. The computer-accessible medium of claim 6, wherein the rule is generated as follows:
For each h in a set of hypotheses H, add h to candidates with a hypothesis being a firing neuron, a keyword, or an ontology term;
    For i=1 to n (where n is a threshold defining a max pattern size), repeat:
        For c in candidates test c →e, for each event e in a set of events E, by counting the instances when a rule does and does not hold, and calculating the rule's posterior odds;
        If rule's odds are greater than the threshold, add the rule to a set of rules;
        Else, remove c from candidates;
    Then, for each c in candidates, add each h in a hypothesis to a copy of the rule, making a new set of candidates, each of length i+1.

10. The computer-accessible medium of claim 6, wherein the at least one rule is a causality rule.

11. The computer-accessible medium of claim 1, wherein the data includes at least one of microarray gene expression data, stock market data, or news data.

12. The computer-accessible medium of claim 6, wherein the at least one rule comprises a temporal logic formula.

13. A method for at least one of organizing or analyzing at least two sets of data comprising:
(a) generating a data structure for the at least two sets of the data, wherein at least one of the sets of the data includes time series data; and
(b) using a processing arrangement, comparing the data structure for the at least two sets of the data, wherein the comparison of the data structure results in one of the at least two sets of data being at least one of organized or analyzed;
wherein the data structure is a Gantt chart, and is generated by the operation of:
Loop for each item in a dataset {
    with w being a chosen size of the time window,
    Collect the average for each collection of columns of width w in a set of columns describing the data's numerical components, starting from a column referred to as 0, average 0 to w, w to 2w and so on until no more columns with numerical data remain),
    For each average computed{
        convert a number to a character representing its level of activity as it relates to 0, and characters being used are U that are greater than zero, D that are less than zero, N that are exactly zero, and I denoting that there is no activity of the entry at that point in time},
    Create an object and store the entry's Unique ID and describing string as defined by a character representations of numerical averages }.

14. The method of claim 13, further comprising generating at least one rule using a rule generating procedure associated with the data structure.

15. The method of claim 14, wherein the at least one rule comprises a temporal logic formula.

16. A system for at least one of organizing or analyzing at least two sets of data comprising a processing arrangement which, when executed, is configured to perform:
(a) generating a data structure for the at least two sets of the data, wherein at least one of the sets of the data includes time series data; and (b) comparing the data structure for the at least two sets of the data, wherein the comparison of the data structure results in one of the at least two sets of data being at least one of organized or analyzed;
wherein the data structure is a Gantt chart, and is generated by the operation of:
Loop for each item in a dataset {
with w being a chosen size of the time window,
Collect the average for each collection of columns of width w in a set of columns describing the data's numerical components, starting from a column referred to as 0, average 0 to w, w to 2w and so on until no more columns with numerical data remain),
For each average computed{
convert a number to a character representing its level of activity as it relates to 0, and characters being used are U that are greater than zero, D that are less than zero, N that are exactly zero, and I denoting that there is no activity of the entry at that point in time},
Create an object and store the entry's Unique ID and describing string as defined by a character representations of numerical averages }.

17. The system of claim 16, wherein the processing arrangement, when executed, is further configured to generate at least one rule using a rule generating procedure associated with the data structure.

18. The system of claim 17, wherein the processing arrangement, when executed, is further configured to test whether the at least one rule satisfies a temporal logic formula.

19. A non-transitory computer-accessible medium having stored thereon computer executable instructions for at least organizing or analyzing at least two sets of data which, when the executable instructions are executed by a processing arrangement, configure the processing arrangement to perform a procedure comprising:
(a) generating a data structure for the at least two sets of the data, wherein at least one of the sets of the data includes time series data; and
(b) comparing the data structure for the at least two sets of the data, wherein the comparison of the data structure results in one of the at least two sets of data being at least one of organized or analyzed;
(c) using a rule generating procedure associated with the data structure, generate at least one rule as follows:
For each h in a set of hypotheses H, add h to candidates with a hypothesis being a firing neuron, a keyword, or an ontology term;
For i=1 to n (where n is a threshold defining a max pattern size), repeat:
For c in candidates test c→e, for each event e in a set of events E, by counting the instances when a rule does and does not hold, and calculating the rule's posterior odds;
If rule's odds are greater than the threshold, add the rule to a set of rules;
Else, remove c from candidates;
Then, for each c in candidates, add each h in a hypothesis to a copy of the rule, making a new set of candidates, each of length i+1.

20. The computer-accessible medium of claim 19, wherein the at least one rule comprises a temporal logic formula.

21. The computer-accessible medium of claim 19, wherein the data structure is a phylogenetic-type tree.

22. A system for at least organizing or analyzing at least two sets of data, comprising:
a hardware processing arrangement configured to:
(a) generate a data structure for the at least two sets of the data, wherein at least one of the sets of the data includes time series data; and
(b) compare the data structure for the at least two sets of the data, wherein the comparison of the data structure results in one of the at least two sets of data being at least one of organized or analyzed;
(c) use a rule generating procedure associated with the data structure, generate at least one rule as follows:
For each h in a set of hypotheses H, add h to candidates with a hypothesis being a firing neuron, a keyword, or an ontology term;
For i=1 to n (where n is a threshold defining a max pattern size), repeat:
For c in candidates test c→e, for each event e in a set of events E, by counting the instances when a rule does and does not hold, and calculating the rule's posterior odds;
If rule's odds are greater than the threshold, add the rule to a set of rules;
Else, remove c from candidates;
Then, for each c in candidates, add each h in a hypothesis to a copy of the rule, making a new set of candidates, each of length i+1.

23. The system of claim 22, wherein the at least one rule comprises a temporal logic formula.

24. The system of claim 22, wherein the data structure is a phylogenetic-type tree.

25. A method for at least organizing or analyzing at least two sets of data, comprising:
(a) generating a data structure for the at least two sets of the data, wherein at least one of the sets of the data includes time series data; and
(b) comparing the data structure for the at least two sets of the data, wherein the comparison of the data structure results in one of the at least two sets of data being at least one of organized or analyzed;
(c) using a rule generating procedure associated with the data structure, generate at least one rule as follows:
For each h in a set of hypotheses H, add h to candidates with a hypothesis being a firing neuron, a keyword, or an ontology term;
For i=1 to n (where n is a threshold defining a max pattern size), repeat:
For c in candidates test c→e, for each event e in a set of events E, by counting the instances when a rule does and does not hold, and calculating the rule's posterior odds;
If rule's odds are greater than the threshold, add the rule to a set of rules;
Else, remove c from candidates;
Then, for each c in candidates, add each h in a hypothesis to a copy of the rule, making a new set of candidates, each of length i+1.

26. The method of claim 25, wherein the at least one rule comprises a temporal logic formula.

* * * * *